(12) United States Patent
Abedini et al.

(10) Patent No.: US 10,283,221 B2
(45) Date of Patent: May 7, 2019

(54) RISK ASSESSMENT BASED ON PATIENT SIMILARITY DETERMINED USING IMAGE ANALYSIS

(71) Applicant: International Business Machines Corporation, Armonk, NY (US)

(72) Inventors: Mani Abedini, Pascoe Vale (AU); Seyedbehzad Bozorgtabar, Carlton (AU); Rajib Chakravorty, Epping (AU); Rahil Garnavi, Macleod (AU)

(73) Assignee: International Business Machines Corporation, Armonk, NY (US)

( * ) Notice: Subject to any disclaimer, the term of this patent is extended or adjusted under 35 U.S.C. 154(b) by 95 days.

(21) Appl. No.: 15/336,252

(22) Filed: Oct. 27, 2016

(65) Prior Publication Data
US 2018/0121626 A1     May 3, 2018

(51) Int. Cl.
G06K 9/00     (2006.01)
G16H 50/30    (2018.01)
G06T 7/00     (2017.01)

(52) U.S. Cl.
CPC .......... G16H 50/30 (2018.01); G06T 7/0014 (2013.01); *G06T 2207/20081* (2013.01); *G06T 2207/30088* (2013.01); *G06T 2207/30096* (2013.01)

(58) Field of Classification Search
None
See application file for complete search history.

(56) References Cited

U.S. PATENT DOCUMENTS

| | | | |
|---|---|---|---|
| 6,075,879 A | 6/2000 | Roehrig et al. | |
| 6,345,275 B2 | 2/2002 | Lee | |
| 6,993,167 B1 | 1/2006 | Skladnev et al. | |
| 7,415,143 B2 | 8/2008 | Grichnik | |
| 7,457,659 B2 | 11/2008 | Maschke | |
| 7,539,334 B2 | 5/2009 | Corrion | |
| 8,837,796 B1 | 9/2014 | Zalutskaya | |
| 9,089,303 B2 | 7/2015 | Chen et al. | |
| 9,092,697 B2 | 7/2015 | Manson et al. | |

(Continued)

FOREIGN PATENT DOCUMENTS

WO     2005060466 A2     7/2005

OTHER PUBLICATIONS melanoma.org, "Melanoma Facts and Statistics," http://www.melanoma.org.au/understanding-melanoma/melanoma-facts-and-statistics/, 2016, 2 pages.

(Continued)

*Primary Examiner* — Stephen P Coleman
(74) *Attorney, Agent, or Firm* — Grant Johnson; Ryan, Mason & Lewis, LLP

(57) ABSTRACT

A method for risk assessment comprises receiving one or more images of a plurality of lesions captured from a body of a target person, generating one or more digital signatures based on the one or more images from the body of the target person, comparing the generated one or more digital signatures to digital signatures of respective reference persons, wherein the comparing comprises measuring similarities between the generated one or more digital signatures and the digital signatures of the respective reference persons, and determining a risk factor for the target person of developing a disease based on the measured similarities and predetermined risk factors of developing the disease for the reference persons.

16 Claims, 13 Drawing Sheets

(56) References Cited

U.S. PATENT DOCUMENTS

| | | |
|---|---|---|
| 2005/0228264 A1 | 10/2005 | Grichnik |
| 2007/0053561 A1 | 3/2007 | Corrion |
| 2007/0100226 A1 | 5/2007 | Yankelevitz et al. |
| 2007/0177786 A1 | 8/2007 | Bartels |
| 2007/0208263 A1 | 9/2007 | John et al. |
| 2011/0123087 A1 | 5/2011 | Nie et al. |
| 2011/0129129 A1* | 6/2011 | Avinash ............. A61B 5/04 382/128 |
| 2011/0218428 A1 | 9/2011 | Westmoreland et al. |
| 2011/0237938 A1 | 9/2011 | Mizuno |
| 2011/0273535 A1 | 11/2011 | Mendelson |
| 2012/0008838 A1 | 1/2012 | Guyon et al. |
| 2014/0142413 A1 | 5/2014 | Chang et al. |
| 2015/0205998 A1* | 7/2015 | Suh ............. G06K 9/00281 382/118 |
| 2015/0302270 A1 | 10/2015 | BenHimane et al. |
| 2016/0157787 A1 | 6/2016 | Merritt et al. |
| 2016/0364529 A1 | 12/2016 | Li et al. |
| 2017/0061621 A1 | 3/2017 | Wortman |
| 2017/0076451 A1* | 3/2017 | Pauly ............. G06F 17/3028 |
| 2018/0075597 A1 | 3/2018 | Zhou et al. |
| 2018/0103932 A1 | 4/2018 | Tahmasebi et al. |

OTHER PUBLICATIONS skincancer.org, "Skin Cancer Facts & Statistics," http://www.skincancer.org/skin-cancer-information/skin-cancer-facts#treatment, Jun. 8, 2016, 6 pages.

A. Scope et al., "The 'Ugly Duckling' Sign: Agreement Between Observers," Journal of Archives of Dermatology, Jan. 2008, pp. 58-64, vol. 144, No. 1.

I. Maglogiannis et al., "Overview of Advanced Computer Vision Systems for Skin Lesions Characterization," IEEE Transactions on Information Technology in Biomedicine, Sep. 2009, pp. 721-733, vol. 13, No. 5.

L.W.C. Chan et al., "Machine Learning of Patient Similarity," IEEE International Conference on Bioinformatics and Biomedicine Workshops, 2010, pp. 467-470.

C.A. Morton et al., "Clinical Accuracy of the Diagnosis of Cutaneous Malignant Melanoma," British Journal of Dermatology, Feb. 1998, pp. 283-287, vol. 138, No. 2.

J.J. Grob et al., "The 'Ugly Duckling' Sign: Identification of the Common Characteristics of Nevi in an Individual as a Basis for Melanoma Screening," Journal of Archives of Dermatology, Jan. 1998, pp. 103-104, vol. 134, No. 1.

List of IBM Patents or Patent Applications Treated as Related.

* cited by examiner

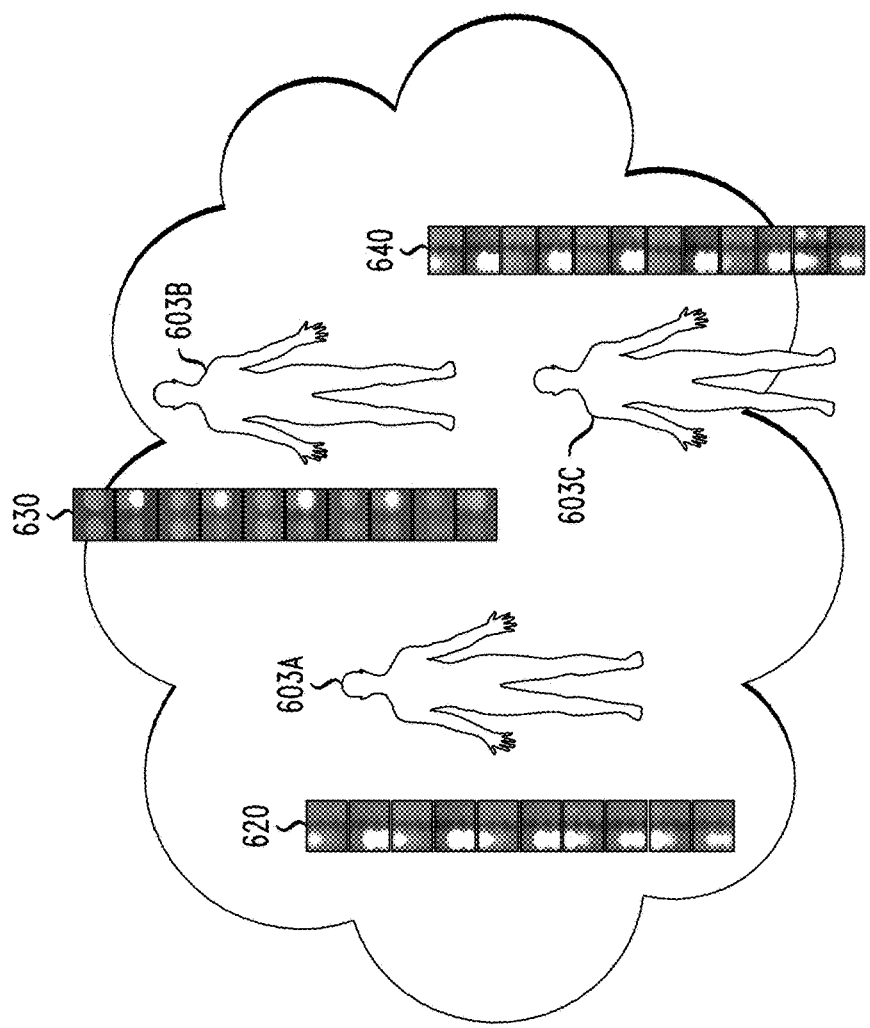
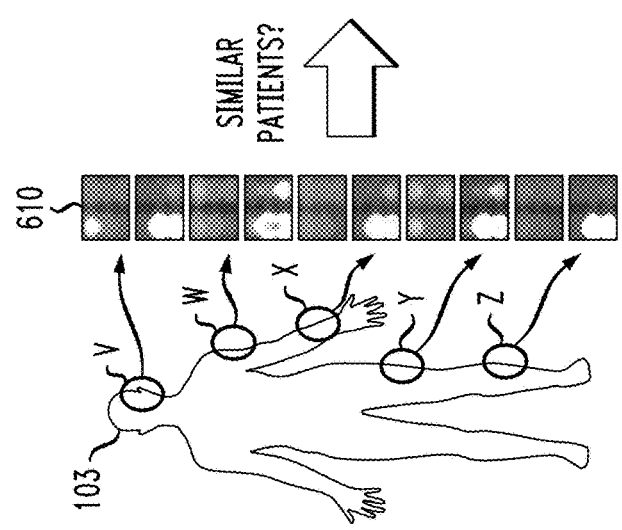
FIG. 6

900

RISK ASSESSMENT BASED ON PATIENT SIMILARITY DETERMINED USING IMAGE ANALYSIS

BACKGROUND

Melanoma is one of the most common cancers in Australian and United States populations. In the United States, 76,380 new cases of invasive melanoma are estimated to be diagnosed in 2016. In 2016, it is estimated that 10,130 people will die of melanoma. The annual cost of treating melanoma is estimated as $3.3 billion. Therefore, besides being fatal, melanoma can affect multiple stages of a societal fabric.

While melanoma can be a fatal disease, it can be treated fully when detected early, by for example, an excisional biopsy. Typically, early detection of melanoma in a skin mole or other lesion is assessed by the presence/absence of certain features in the mole or other lesion. These examinations are usually formed as defined protocols used by health care professionals. There exist several such protocols such as, for example, "ABCD Rule", "Menzies Rule", "3 point checklist", etc. Common features across these different protocols can include the presence of certain "colors" (brown, black, red, etc.) and/or patterns (networks, globules, etc.). When examined under dermoscopy or other clinical imagery, health care professionals look for signatures and assign a score to the mole or other lesion. The decision to perform a biopsy occurs if the score exceeds a predefined threshold, the value of which may vary depending on rules and/or protocols.

In skin cancer diagnosis, risk analysis is also an important step. Dermatologists or other health care professionals evaluate a patient's risk of getting skin cancer based on factors such as, for example, age, gender, family history, and/or lifestyle. However, in current practice, the properties of skin and lesion patterns as they relate to patient risk factor are not considered.

SUMMARY

According to an exemplary embodiment of the present invention, a method for risk assessment comprises receiving one or more images of a plurality of lesions captured from a body of a target person, generating one or more digital signatures based on the one or more images from the body of the target person, comparing the generated one or more digital signatures to digital signatures of respective reference persons, wherein the comparing comprises measuring similarities between the generated one or more digital signatures and the digital signatures of the respective reference persons, and determining a risk factor for the target person of developing a disease based on the measured similarities and predetermined risk factors of developing the disease for the reference persons.

According to an exemplary embodiment of the present invention, a system for risk assessment comprises a memory and at least one processor coupled to the memory, wherein the at least one processor is configured to receive one or more images of a plurality of lesions captured from a body of a target person, generate one or more digital signatures based on the one or more images from the body of a target person, compare the generated one or more digital signatures to digital signatures of respective reference persons, wherein the processor is further configured to measure similarities between the generated one or more digital signatures and the digital signatures of the respective reference persons, and determine a risk factor for the target person of developing a disease based on the measured similarities and predetermined risk factors of developing the disease for the reference persons.

According to an exemplary embodiment of the present invention, a computer program product for risk assessment comprises a computer readable storage medium having program instructions embodied therewith, the program instructions executable by a processor to cause the processor to perform a method comprising receiving one or more images of a plurality of lesions captured from a body of a target person, generating one or more digital signatures based on the one or more images from the body of the target person, comparing the generated one or more digital signatures to digital signatures of respective reference persons, wherein the comparing comprises measuring similarities between the generated one or more digital signatures and the digital signatures of the respective reference persons, and determining a risk factor for the target person of developing a disease based on the measured similarities and predetermined risk factors of developing the disease for the reference persons.

These and other exemplary embodiments of the invention will be described or become apparent from the following detailed description of exemplary embodiments, which is to be read in connection with the accompanying drawings.

BRIEF DESCRIPTION OF THE DRAWINGS

Exemplary embodiments of the present invention will be described below in more detail, with reference to the accompanying drawings, of which:

FIG. 6 is a diagram illustrating identification of similar patients, according to an exemplary embodiment of the present invention.

DETAILED DESCRIPTION

Exemplary embodiments of the invention will now be discussed in further detail with regard to image analysis and, in particular, to using image analysis to assess risk based on patient similarity. This invention may, however, be embodied in many different forms and should not be construed as limited to the embodiments set forth herein.

Embodiments of the present invention relate to systems and methods which find similar of patients based on lesion image assessment. In accordance with an embodiment of the present invention, patients are categorized with cohorts based on their skin lesion patterns, and the cohorts' levels of risk of acquiring cancer are used by a health care professional to assess the cancer risk of patients having similar lesion profiles.

Embodiments of the present invention relate to systems and methods to identify similar patients based on the assessment of lesion images from a body scan, such as, for example, a full or partial body scan. In accordance with an embodiment of the present invention, health care professionals are able to quantify cancer risk based on analysis of the skin and lesion images taken from a patient, along with previous observations, including, data, images, and patient profiles saved in, for example a database. In order to build key visual points for comparing individuals, a system according to an embodiment of the present invention, builds mole digital signatures (MDSs) and uses a hybrid deep learning and sparse coding approach. More specifically, a system and method for generating MDSs identifies patients similar to a target patient and uses their images and information to calculate a cancer risk level for the target patient. In accordance with an embodiment of the present invention, the risk levels can be categorical or continuous numbers generated from a regression model.

In connection with generating an MDS, sparse coding and auto encoder methods are used to leverage deep learning methods and discriminative feature vectors to compute similarity. To determine similarity, the systems and methods consider meta-data, such as, but not necessarily limited to, age, gender, geographical data, socio-economic data, and/or lifestyle (e.g., frequency of sunscreen application), along with MDSs for target and cohort patients.

Figure 1:
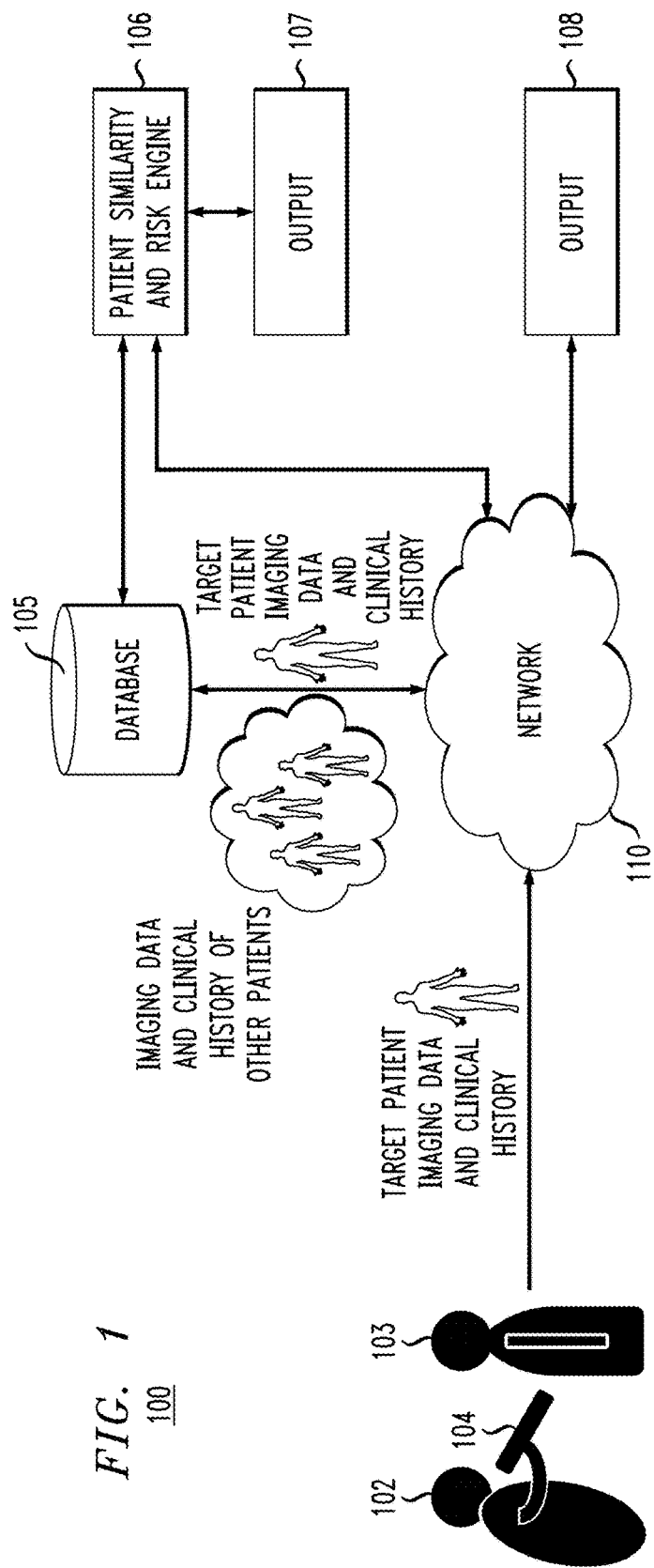
FIG. 1 is block diagram illustrating a system for risk assessment based on patient similarity, according to an exemplary embodiment of the present invention.

FIG. 1 is block diagram illustrating a system for risk assessment based on patient similarity, according to an exemplary embodiment of the present invention. As shown in FIG. 1 by lines and/or arrows, the components of the system 100 are operatively connected to each other via, for example, physical connections, such as wired and/or direct electrical contact connections, and/or wireless connections, such as, for example, WiFi, BLUETOOTH, IEEE 802.11, and/or networks, including but not limited to, a local area network (LAN), wide area network (WAN), cellular network, ad hoc networks, WANET, satellite network or the Internet. For example, a network 110 can operatively link components 104, 105, 106, 107 and 108 of the system 100.

By way of non-limiting example, in accordance with an embodiment of the present invention, referring to FIG. 1, the system includes at least one capture device 104 that is used by, for example, a practitioner 102, such as a doctor, nurse, physician's assistant, technician, etc., to capture images of any lesions and/or groups of lesions from a target patient 103. The capture device 104 can include, but is not necessarily limited to, a camera, such as a still picture or video camera, scanner, specialized imaging device, tablet, and/or smart mobile device, such as a smart phone or tablet that can, for example, take a picture or perform a full body or partial body scan of a target patient 103. The capture device 104 can be further used to receive meta data inputs and/or sense meta data, the meta data including, for example, patient information, history, age, skin tone, and/or location on the body of respective lesions or groups of lesions. The capture device 104 can be configured to communicate wirelessly with the other components 105-108 of the system 100 over the network 110.

The database 105 can be used to store the meta data and images of lesions and/or groups of lesions that have been taken from a target patient 103. The database 105 also stores patient information and images and data concerning the images that have been obtained from a number of patients over time who may have been subject to risk analysis and/or cancer treatment at some point in time. The patient information, images and image data in the database 105 may be used in connection with a risk analysis of the target patient 103. The lesion images produced in accordance with embodiments of the present invention include, but are not necessarily limited to, dermoscopy, sonography, confocal microscopy, multiphoton tomography, or optical coherence tomography images.

The database 105 can be, for example, cloud-based. The data and images from the database 105 are electronically accessible by a patient similarity and risk engine 106, for example, via the network 110 or directly, and are used by the patient similarity and risk engine 106 when determining target patient similarity to other (reference) patients and analyzing risk based on the similarity. The database 105 is also configured to receive images and meta data from the capture device 104, or other sources of patient images and data, via network 110 or directly.

The system 100 further includes the patient similarity and risk engine 106, which generates target patient MDSs and images and data to determine patient similarity and risk based on the images and data of the target and reference patients. The patient similarity and risk engine 106 provides results to one or more output devices 107 and 108 either directly or via a network 110 so that a user, such as, for example, a practitioner 102 or other medical personnel, can view the determinations made by the patient similarity and risk engine 106 and decide on a treatment protocol for a target patient 103. The output devices 107 and 108, can include, for example, a desktop or portable computer, tablet, personal digital assistant (PDA), smart phone or other computing device having an interface for viewing the results. According to an embodiment, the results can be transmitted to the capture device 104, which can also function as an output device. The patient similarity and risk engine 106 also transmits analysis results to the database 105, so that the database 105 can electronically store, and the patient similarity and risk engine 106 can electronically access these results from the database 105 when performing subsequent analyses as explained in more detail herein. The patient similarity and risk engine 106 is explained in further detail herein in connection with FIG. 2.

Figure 2:
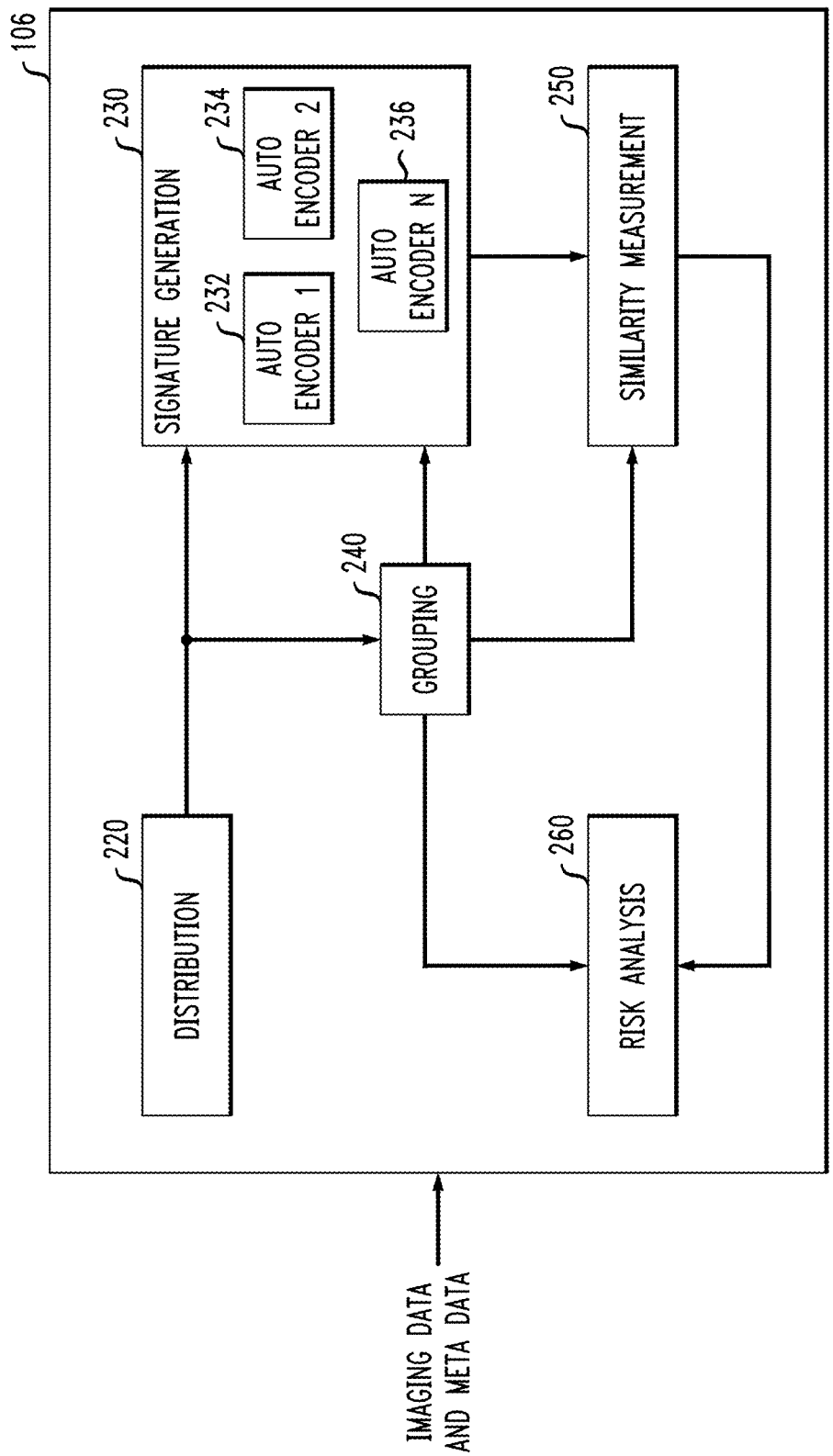
FIG. 2 is a block diagram illustrating a patient similarity and risk engine in a system for risk assessment based on patient similarity, according to an exemplary embodiment of the present invention.
Figure 3:
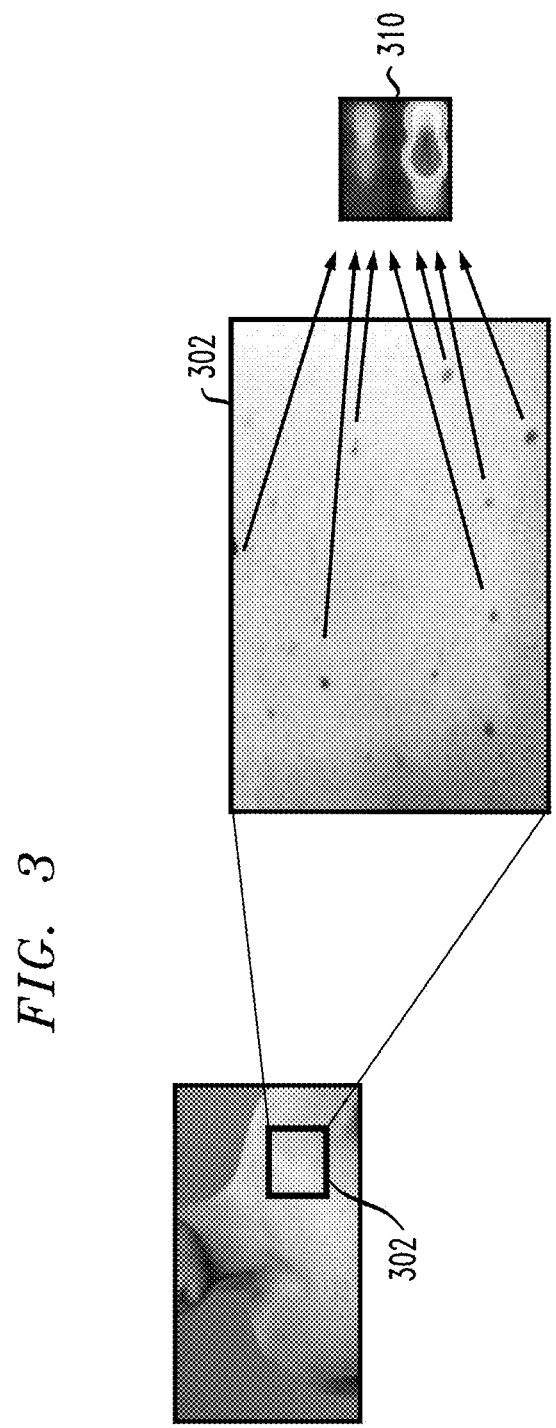
FIG. 3 is a diagram showing capturing of an image from a site on a body of a patient and generation of a mole digital signature for the site, according to an exemplary embodiment of the present invention.

FIG. 2 is a block diagram illustrating a patient similarity and risk engine 106, according to an exemplary embodiment of the present invention. Referring to FIG. 2, the patient similarity and risk engine 106 includes a distribution module 220, a signature generation module 230, a grouping module 240, a similarity measurement module 250 and a risk analysis module 260. The patient similarity and risk engine 106 receives imaging data and meta data of the target patient 103 and other (reference) patients, which can be transmitted to the patient similarity and risk engine 106 from the capture device 104 and the database 105, for example, via network 110. The imaging and meta data of the target patient 103 includes, for example, lesion images from different locations on the target patient's body. For example, referring to FIG. 3, an image of a plurality of lesions can be taken from a location 302 on the patient, and a mole digital signature (MDS) 310 can be generated for the plurality of lesions at location 302. Similar images can be captured from other locations on the patient. The meta data of the target patient 103 can include, for example, data about the images, such as location on the body, and factors that may be considered relevant when assessing a risk of cancer, such as, age, gender, race, geographic location, behavior, family history, etc. Imaging data and meta data of other (reference) patients can include MDSs and information about the reference patients, such as, for example, age, gender, race, geographic location, behavior, family history, etc.

Figure 5:
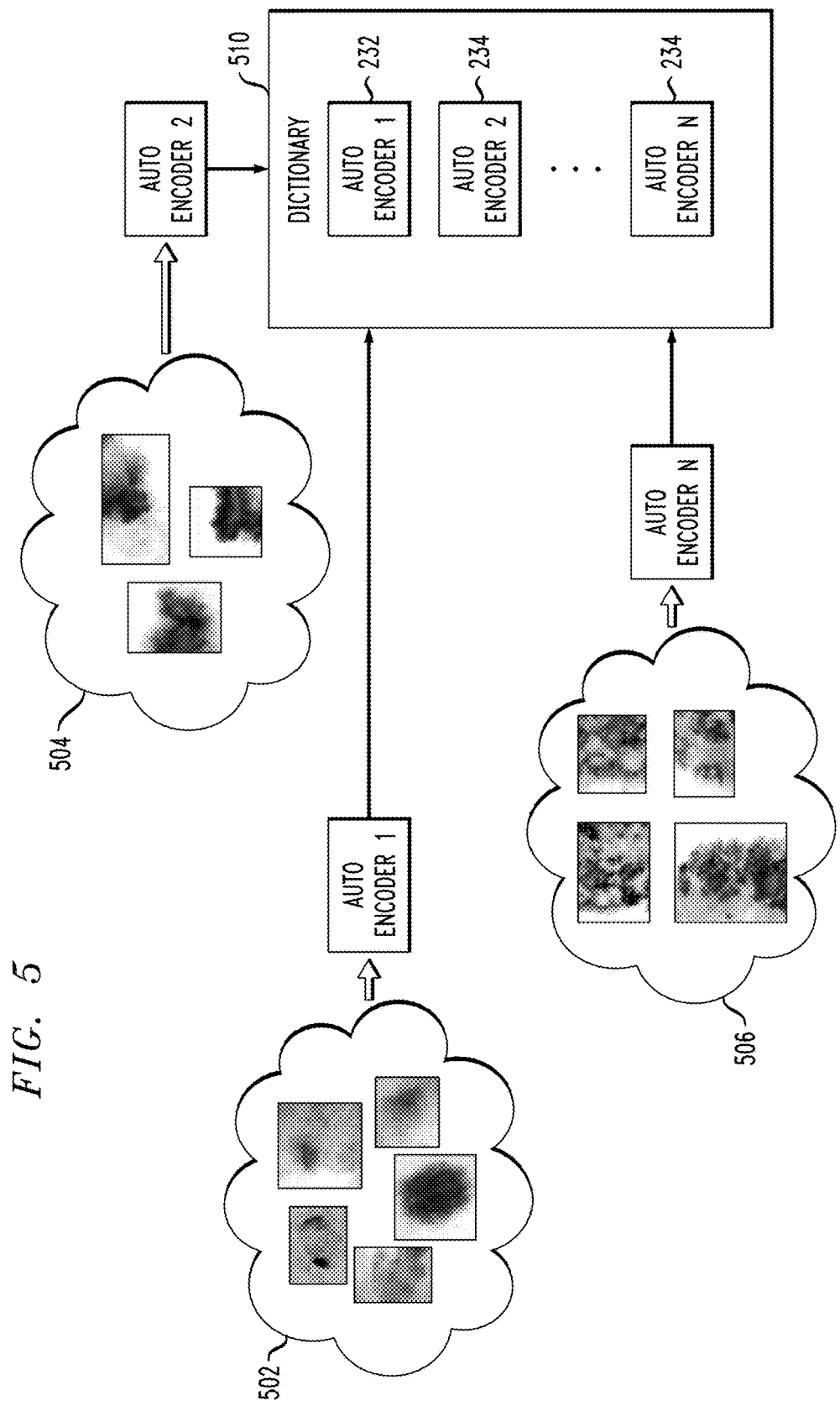
FIG. 5 is a diagram illustrating training of auto encoders for respective groups of patients, according to an exemplary embodiment of the present invention.

The distribution module 220 receives the imaging and meta data and transmits the imaging and meta data to signature generation and grouping modules 230 and 240. In accordance with an embodiment of the present invention, the grouping module 240 uses patient characteristics, such as, for example, age, gender, race, geographic location, behavior, family history, etc., to build groups of non-target patients, which are sent to the signature generation module 230. For each group, an auto encoder, such as, auto encoder 1 (232), auto encoder 2 (234) . . . auto encoder N (236) is trained. The number N of auto encoders can vary based on the number of groups. Referring, for example, to FIG. 5, each group 502, 504 and 506 can have a plurality of images from multiple patients in the group. By way of non-limiting example, a group can correspond to hundreds or thousands of patients, and include hundreds of thousands of images from multiple locations on the patients. The images or groups of images used for training the auto encoders 1, 2, . . . N corresponding to each group already have digital signatures. The dictionary 510 is the collection of all trained auto encoders 232, 234, 236 (N auto encoders).

Figure 4A:
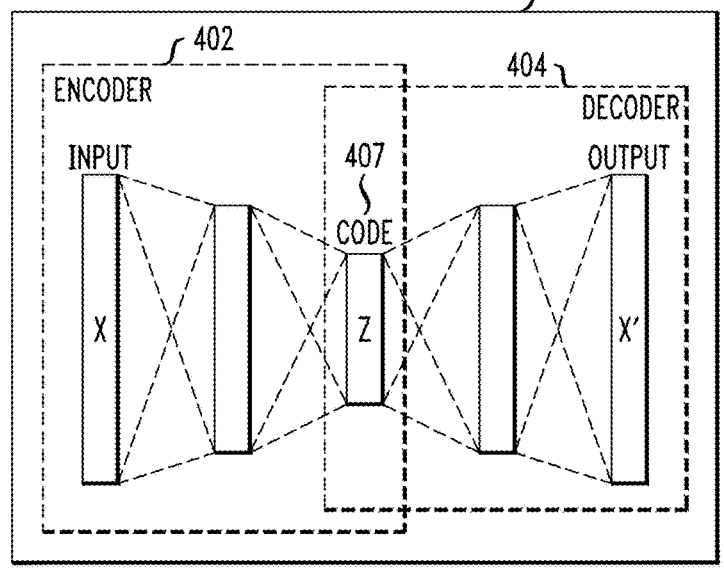
FIGS. 4A and 4B are diagrams illustrating components and functioning of an auto encoder, according to an exemplary embodiment of the present invention.

When a new lesion image or set of lesion images of a target patient 103 is captured and received by the signature generation module 230 via the distribution module 220, each auto encoder 1, 2, . . . N (232, 234, 236) is used to generate a code forming part of the digital signature for an image or set of images. More specifically, referring to FIGS. 4A and 4B, each auto encoder 232/234/236 includes an encoder 402 and a decoder 404, and learns feature representations automatically (unsupervised) from data. The encoder 402 learns codes (e.g., basic features), which can be used by the decoder 404 to reconstruct the original image, while minimizing construction error. For example, the encoder 402 of each auto encoder 232/234/236 encodes an image 437 into a smaller sized vector (fixed sized vector of size m), and the decoder 404 performs a reconstruction (decoding) to result in the image 439. As a result, the data structure of image 437 is digitally transformed into the digitally reconstructed image 439 based on code 407.

When creating a patient's digital signature, a system in accordance with an embodiment of the present invention is learning the codes 407 to reconstruct images of individual lesions and/or images of groups of lesions. More specifically, an auto encoder learns to encode and decode an image by reconstructing the original image from the code 407. An auto encoder requires a substantial number of training samples to learn an encoding algorithm. Digital signatures of images of individual lesions and/or images of groups of lesions include collection of the results of applying all auto encoders 1, 2, . . . N to an image and/or group of images. Each auto encoder 1, 2, . . . N generates a code and collectively this results in a matrix of codes. For example, a matrix of N×m is produced, which is the MDS. N is an integer representing the number of auto encoders, and m is an integer representing the size of the vector in the hidden (e.g., middle) layer of the auto encoder, also referred to herein as the length of the code.

Figure 4B:
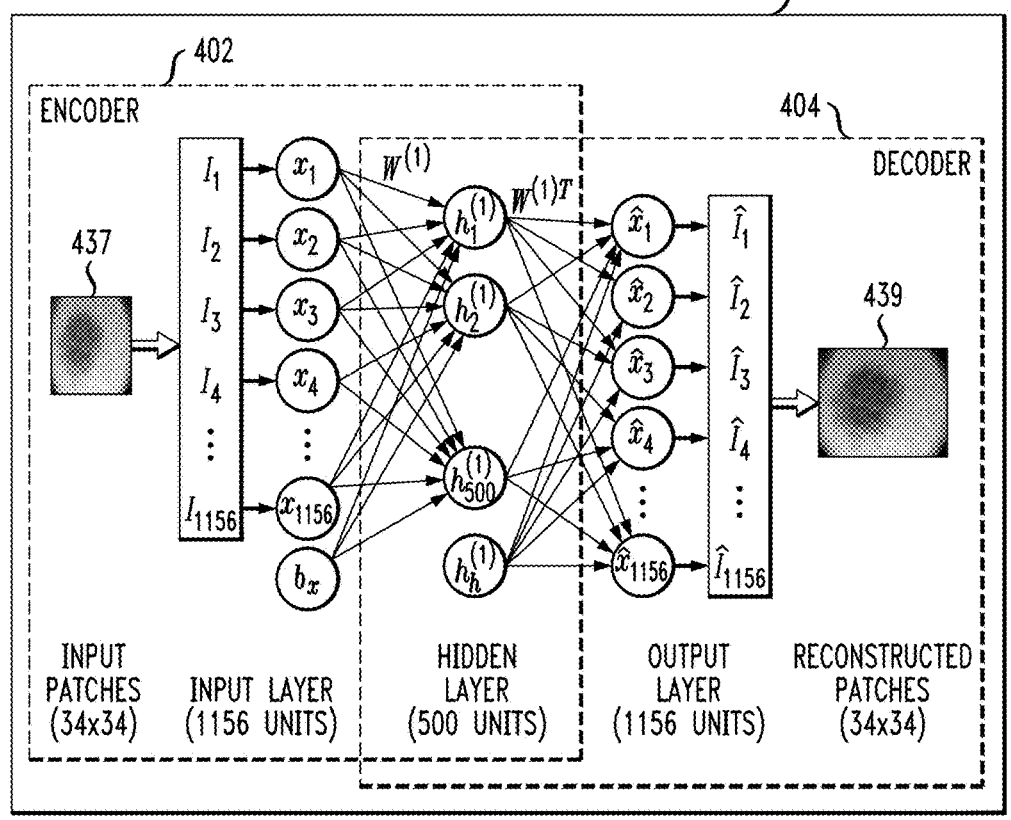

Referring to FIG. 4B, the hidden layer provides the code 407. In the example in FIG. 4B, an image 437 with 34×34 resolution has 1156 pixels (units) is decoded into image 439 also with 34×34 resolution and 1156 pixels (units) by using 500 pixel code (the size m of hidden layer). The output of each unit in the hidden layer is a floating point number between 0 and 1.

Depending on what images are captured and how the images are processed, a digital signature can represent moles from a specific region on the body and/or moles from multiple locations of the body of a patient. For example, according to an embodiment of the present invention, auto encoding through each auto encoder 1, 2, . . . N is performed separately for images from each site/body part. This takes into consideration that, for a particular patient, lesions of different sites (body parts) are can be visually different. Referring back to FIG. 3, element 310 is an example of an image representing a digital signature for a patient in connection with a plurality of lesions at a particular site on a body of a patient.

As a result, auto encoders are customized based on sites. According to an alternative embodiment, the collection of auto encoders 1, 2, . . . N is for an entire body, regardless of site/body part.

At some point the auto encoders 1, 2, . . . N are considered trained, and do not have to be trained each time digital signatures are being generated for a particular patient. However, auto encoders can be updated over time, but not necessarily for each patient.

Referring back to FIG. 2 and to FIG. 6, a similarity measurement module 250 compares the generated digital signatures of the target patient 103 from the signature generation module 230 to digital signatures of the reference patients 603A, 603B and 603C to determine patient similarity based on images of the target patient and reference patients whose images and meta data were received and distributed to the grouping module 240 by the distribution module 220 of the patient similarity and risk engine 106. Three reference patients 603A-C are shown for purposes of example only, and the embodiments of the present invention are not limited thereto. More than or less than three reference patients may be considered. For example, embodiments of the present invention may consider thousands of reference patients.

Referring to FIG. 6, each circled portion V, W, X, Y, Z on different sites of patient 103 can have one or more lesions, and the signature generation module 230 generates mole digital signatures per each site (body part), which is represented by element 610. Each box 610 represents a mole digital signature. For example, each box 610 represents a matrix of N×m, the result of running N auto encoders with the output of vector m. The same process is repeated for each body site. If more than one lesion exists in a site (body part) an arithmetic average over the multiple mole signatures is taken to generate a generic body site mole signature. In other words, in the case of having more than one lesion per site, the system averages multiple mole signatures of a site to generate a representative signature for the site.

Embodiments of the present invention operate based on the premise that similar visual skin properties lead to similar biological/genetic mechanisms, and, therefore, perform a comparison analysis for similar visual patterns to predict biological/medical risk factors. More specifically, referring to FIG. 6, similar patients are identified based on biological blueprints which are represented by a plurality of mole digital signatures (MDSs) of patients. For example, a plurality of MDSs 620, 630 and 640 corresponding to multiple sites for each patient 603A, B and C, respectively, are compared to the MDSs for the target patient 103 to determine similarities if any. The MDSs of the reference patients considered for similarity can be preexisting and retrieved from a database, such as database 105. The determination of which patients are looked at in order to determine similarity with the target patient is based on an initial determination of similarity between digital signatures. Alternatively, any narrowing down to determine which patients are looked at for purposes of determining similarity to the target patient 103 may also consider meta data associated with the patients (e.g., age, gender, behavior, geography, etc.) that may categorize the patients into the same or similar groups as the target patient.

Figure 7:
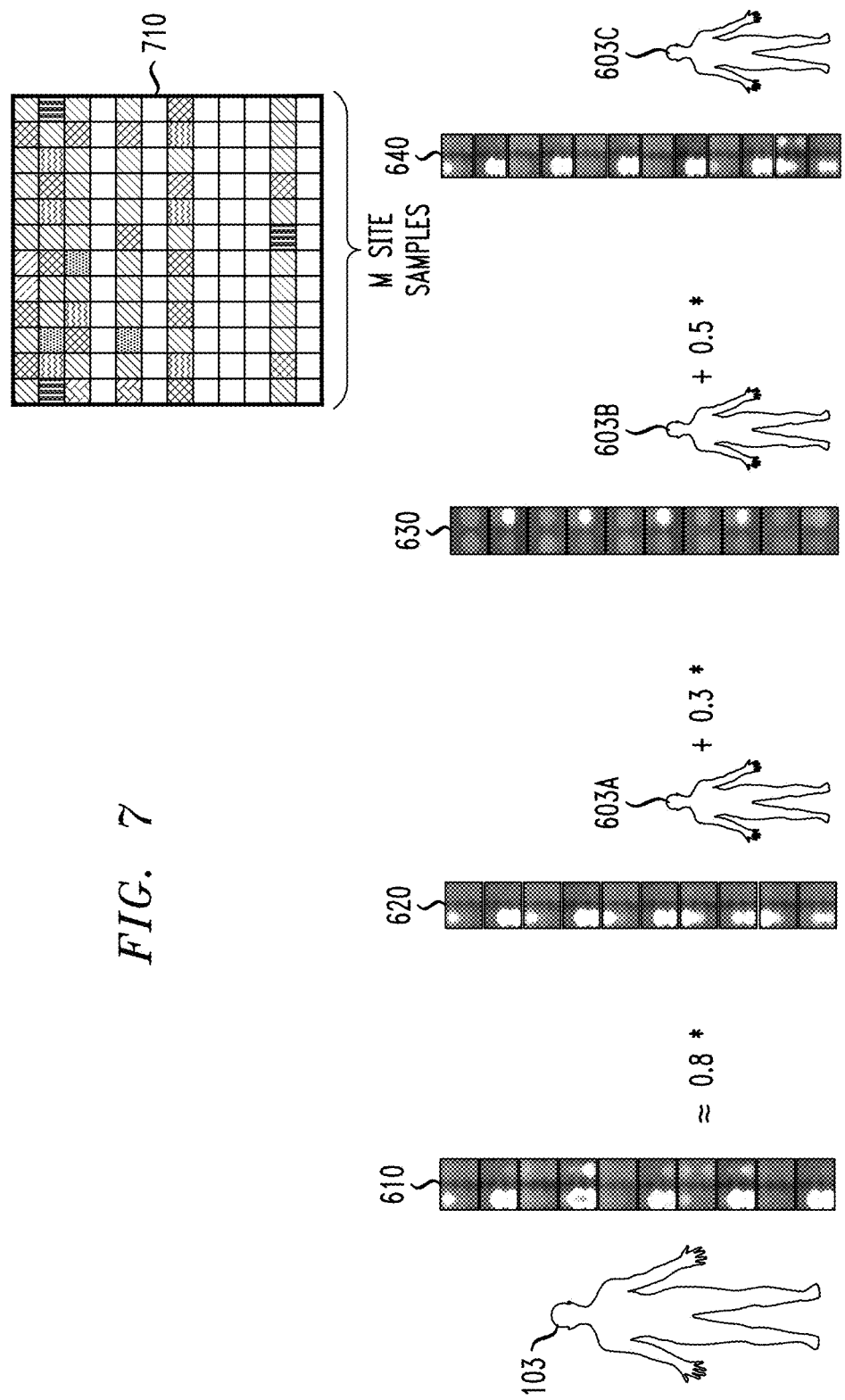
FIG. 7 is a diagram illustrating a linear combination of patients representing a target patient signature, according to an exemplary embodiment of the present invention.

Referring to FIG. 7, sparse coding methods are used to determine similar patients. FIG. 7 illustrates a sparse representation 710 of the signatures for the target patient 103 (e.g., M signatures based on M sites). Sparse representation 710 is color coded representation, wherein the number of columns correspond to a number of body parts (sites), which in FIG. 7, is illustrated as M sites. Each row corresponds to a patient with lesions from M sites. Accordingly, each element in a row is actually a mole digital signature 610 of patient corresponding to a site, as explained above.

Based on sparse coding methods, the digital signatures of the target patient 103 can be represented by linear combination of digital signatures of K patients, where K is an integer greater than 1. For example, as shown in FIG. 7, the digital signatures of target patient 103 are represented by the linear combination of digital signatures of similar patients 603A, 603B and 603C, where the digital signatures of patient 603A are given the highest weight (0.8 or 80%) due to the most similarity to the digital signatures of target patient 103, and the digital signatures of patient 603B are given the lowest weight (0.3 or 30%) due to the least similarity to the digital signatures of target patient 103 in the particular grouping of K patients. Sparse coding defines the linear combination of digital signatures to generate a target patient signature. The fusion weights are given by sparse coding, which represent a similarity level.

Figure 8:
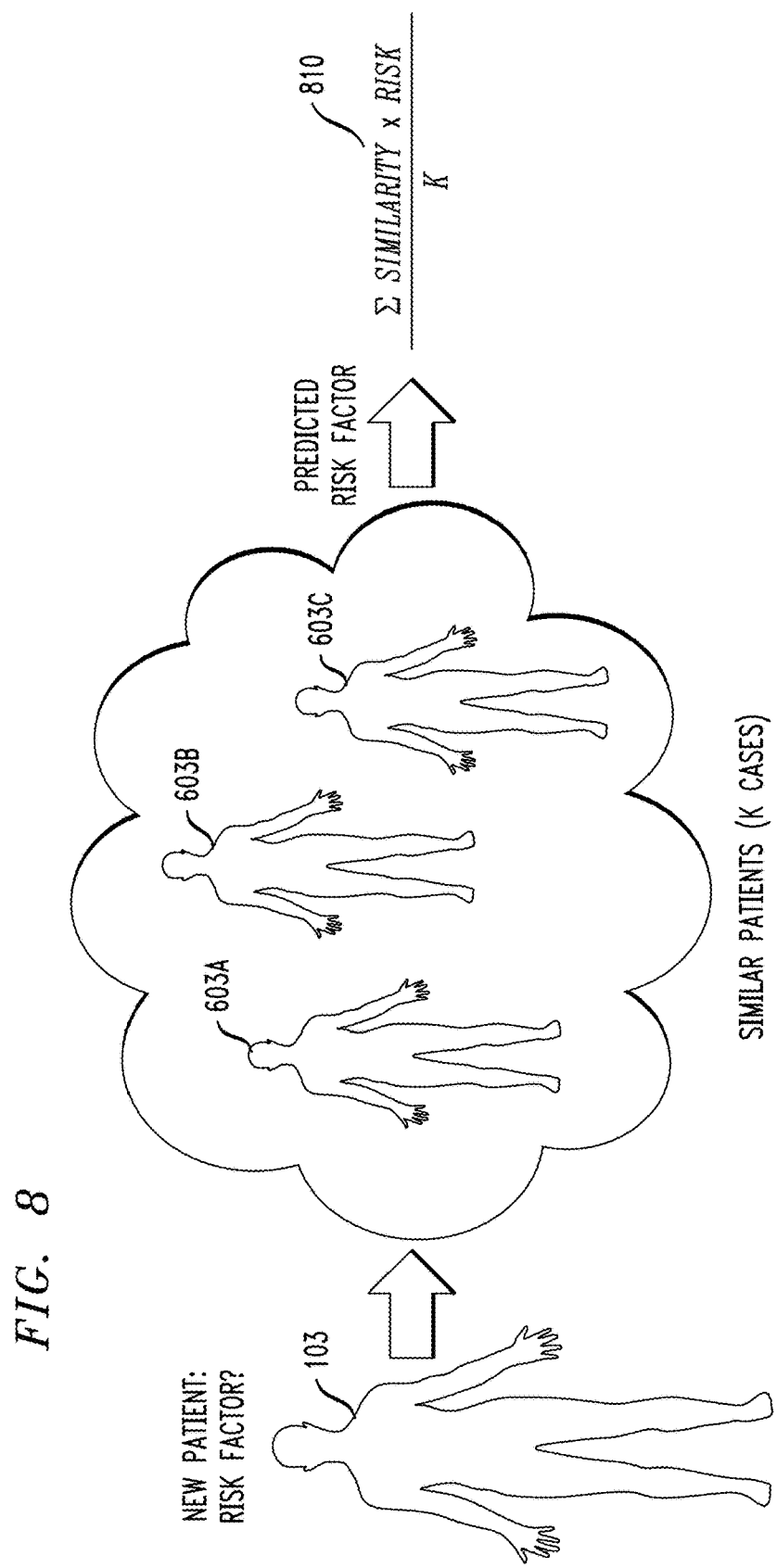
FIG. 8 is a diagram illustrating risk analysis of a target patient based on comparisons to similar patients, according to an exemplary embodiment of the present invention.

Referring back to FIG. 2 and to FIG. 8, a risk analysis module 260 determines a risk factor for the target patient to be used when assessing the target patient's risk for getting skin cancer. The risk analysis module 260 takes into consideration the target patient's similarity with other (reference) patients determined by the similarity measurement module 250, and corresponds to the similarity with known risk factors of getting skin cancer of the other patients. For example, referring to FIG. 8, the risk factor for target patient 103 is the sum of known (e.g., predetermined) risk factors for each patient 603A, 603B and 603C of getting skin cancer multiplied by a weighted value for similarity of each patient 603A, 603B and 603C to target patient 103 found via the image analysis using the deep learning and sparse coding approaches described herein. The predicted risk factor is given by the following formula (1):

$$\frac{\sum \text{Similarity} \times \text{Risk}}{K} \qquad (1)$$

where Similarity is weighted similarity (e.g. 10%, 20%, 30%, etc.) of each patient (1, 2, ... K) to a target patient, Risk is a normalized risk factor (e.g., 0-1, 0-100, etc.) for each patient (1, 2, ... K), and K is the number of patients considered similar to the target patient, where K is an integer greater than 1. The value for Similarity is the same as the weights in the linear combination found using sparse coding.

Figure 9:
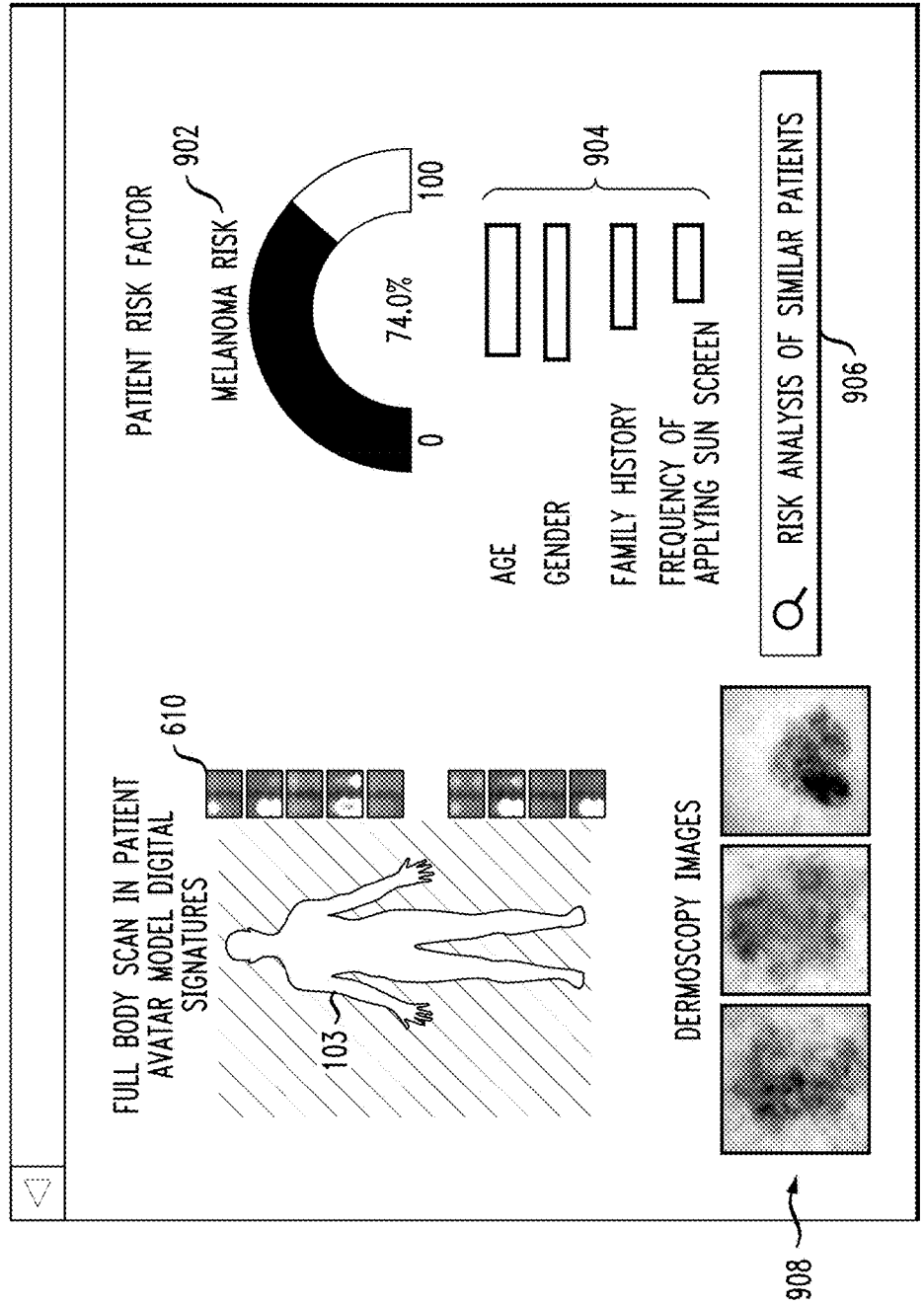
FIG. 9 is a diagram illustrating a user interface indicating risk analysis results, according to an exemplary embodiment of the present invention.

Referring, for example, to FIG. 9, which illustrates a user interface 900 indicating risk analysis results, the predicted risk factor is used to generate an overall risk factor 902 for the target patient of getting skin cancer. The user interface 900 further includes, for example, information about the target patient 904, which can include, but is not necessarily limited to, age, gender, family history of cancer, and/or behavior information (e.g., frequency of applying sunscreen). The interface 900 can include a field 906 to permit a user to search for risk analyses of similar patients, as well as selected lesion dermoscopy images 908, an avatar, and mole digital signatures 610 per each site (body part) of the patient 103.

As used herein, term "real-time" refers to output within strict time constraints. Real-time output can be understood to be instantaneous or on the order of milliseconds or microseconds. Of course, it should be understood that depending on the particular temporal nature of the system in which an embodiment of the invention is implemented, other appropriate timescales that provide approximately contemporaneous performance and output can be achieved. In accordance with embodiments of the present invention, a determination of patient similarity and a corresponding risk factor for a target patient based on lesion images of the target patient and outputting the result to an end user can be performed in real-time upon capturing one or more lesion images for a patient 103 and transmitting the one or more lesion images to the patient similarity and risk engine 106 for analysis. In accordance with an embodiment of the present invention, a practitioner can receive an automated alert transmitted via, for example, a communication network, that there has been a determination of patient similarity and a corresponding risk factor for a target patient, along with the ability to view the determination results, including, for example, digital representations of MDSs and reconstructed lesion images.

Figure 10:
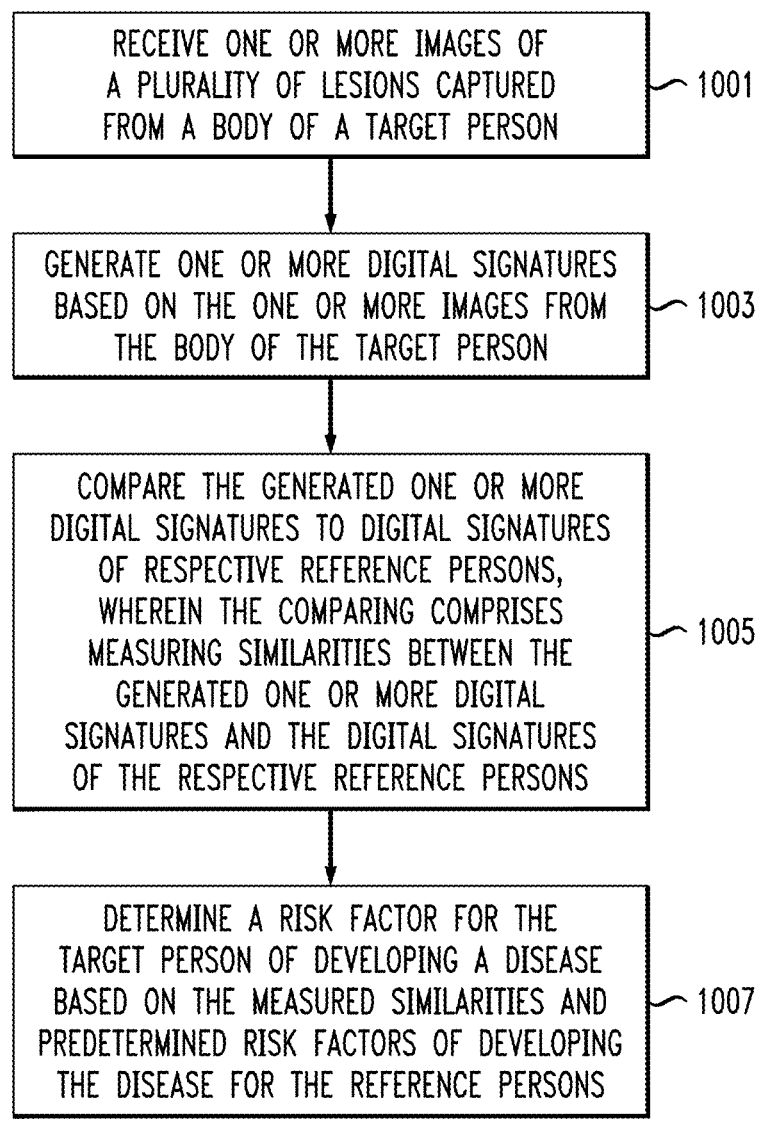
FIG. 10 is a flow diagram of a process for risk assessment based on patient similarity, according to an exemplary embodiment of the invention.

FIG. 10 is a flow diagram of a process for risk assessment based on patient similarity, according to an exemplary embodiment of the invention. Referring to FIG. 10, the process 1000 includes, at block 1001, receiving one or more images of a plurality of lesions captured from a body of a target person. For example, as noted in connection with FIG. 1, a capture device 104 can capture images of lesions from different parts of the body of a target patient 103, and transmit the captured images via, for example, a network 110, to a patient similarity and risk engine 106 where the images are received.

At block 1003, one or more digital signatures are generated based on the one or more images from the body of the target person. According to an embodiment of the present invention, the method may also comprise separating the reference persons into a plurality of groups based on one or more characteristics (e.g., age, gender, race, geographic location, behavior, and/or family history, etc.) of the reference persons, and training an auto encoder for each group of the plurality of groups. Training can be performed using lesion images of the reference persons for each group.

Generating the one or more digital signatures includes processing the one or more images from the body of the target person with each trained auto encoder to generate respective codes corresponding to each trained auto encoder. A digital signature may include a matrix of the respective codes, and the processing may be performed separately for images from different regions on the body of the target person. A digital signature can also correspond to a region on the body of the target person.

The process 1000 further includes, at block 1005, comparing the generated one or more digital signatures to digital signatures of respective reference persons. The comparing comprises measuring similarities between the generated one or more digital signatures and the digital signatures of the respective reference persons, which can be performed using sparse coding. According to an embodiment of the present invention, based on the results of the sparse coding, the method can further include defining the generated one or more digital signatures of the target patient as a linear combination of the digital signatures of the respective reference persons.

The process 1000 further includes, at block 1007, determining a risk factor for the target person of developing a disease (e.g., skin cancer) based on the measured similarities and predetermined risk factors of developing the disease for the reference persons. Determining the risk factor can include calculating a summation of the predetermined risk factors with respect to each reference person, wherein each of the predetermined risk factors is adjusted based on a value for similarity between the generated one or more digital signatures of the target patient and one or more digital signatures of each reference patient.

Embodiments of the present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 11:
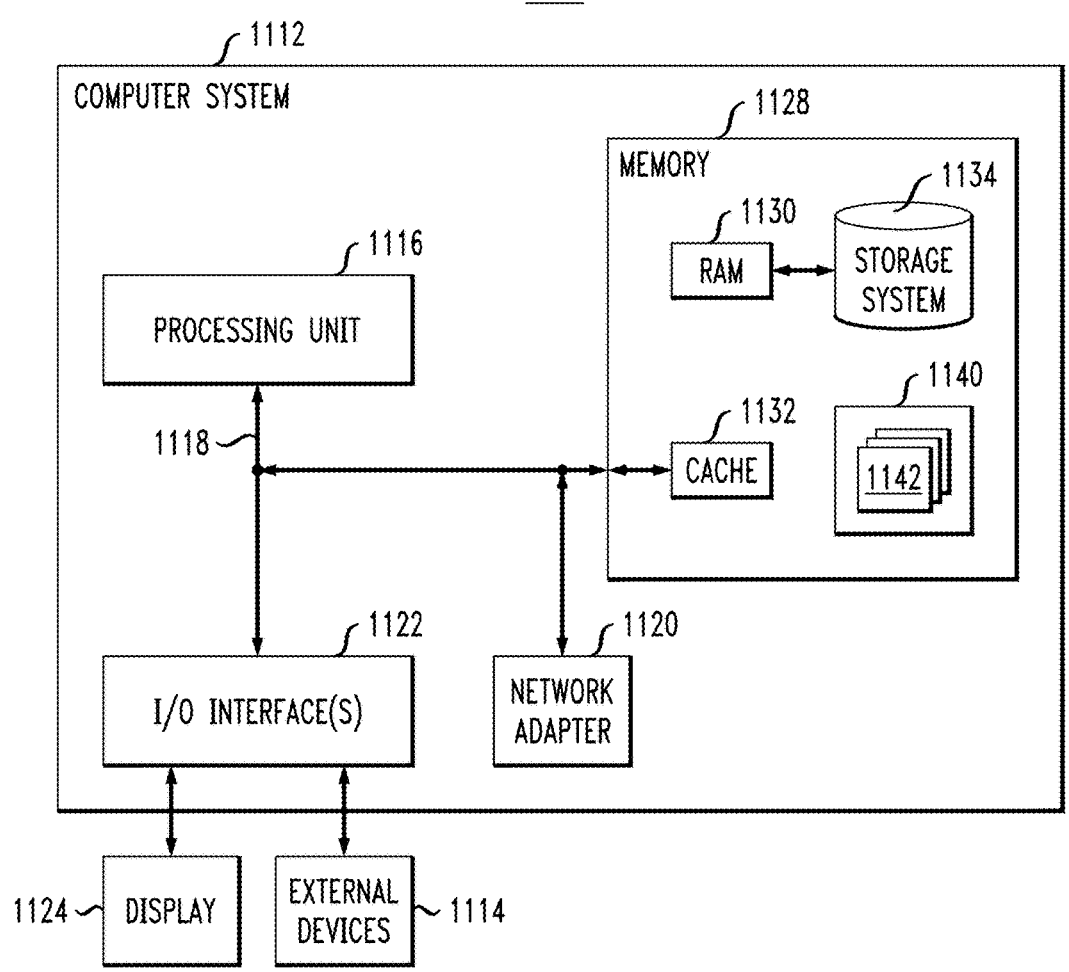
FIG. 11 illustrates a computer system in accordance with which one or more components/steps of the techniques of the invention may be implemented, according to an exemplary embodiment of the invention.

One or more embodiments can make use of software running on a general-purpose computer or workstation. With reference to FIG. 11, in a computing node 1110 there is a computer system/server 1112, which is operational with numerous other general purpose or special purpose computing system environments or configurations. Examples of well-known computing systems, environments, and/or configurations that may be suitable for use with computer system/server 1112 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 1112 may be described in the general context of computer system executable instructions, such as program modules, being executed by a computer system. Generally, program modules may include routines, programs, objects, components, logic, data structures, and so on that perform particular tasks or implement particular abstract data types. Computer system/server 1112 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 11, computer system/server 1112 in computing node 1110 is shown in the form of a general-purpose computing device. The components of computer system/server 1112 may include, but are not limited to, one or more processors or processing units 1116, a system memory 1128, and a bus 1118 that couples various system components including system memory 1128 to processor 1116.

The bus 1118 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The computer system/server 1112 typically includes a variety of computer system readable media. Such media may be any available media that is accessible by computer system/server 1112, and it includes both volatile and non-volatile media, removable and non-removable media.

The system memory 1128 can include computer system readable media in the form of volatile memory, such as random access memory (RAM) 1130 and/or cache memory 1132. The computer system/server 1112 may further include other removable/non-removable, volatile/nonvolatile computer system storage media. By way of example only, storage system 1134 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 1118 by one or more data media interfaces. As depicted and described herein, the memory 1128 may include at least one program product having a set (e.g., at least one) of program modules that are configured to carry out the functions of embodiments of the invention. A program/utility 1140, having a set (at least one) of program modules 1142, may be stored in memory 1128 by way of example, and not limitation, as well as an operating system, one or more application programs, other program modules, and program data. Each of the operating system, one or more application programs, other program modules, and program data or some combination thereof, may include an implementation of a networking environment. Program modules 1142 generally carry out the functions and/or methodologies of embodiments of the invention as described herein.

Computer system/server 1112 may also communicate with one or more external devices 1114 such as a keyboard, a pointing device, a display 1124, etc., one or more devices that enable a user to interact with computer system/server 1112, and/or any devices (e.g., network card, modem, etc.) that enable computer system/server 1112 to communicate with one or more other computing devices. Such communication can occur via Input/Output (I/O) interfaces 1122. Still yet, computer system/server 1112 can communicate with one or more networks such as a local area network (LAN), a general wide area network (WAN), and/or a public network (e.g., the Internet) via network adapter 1120. As depicted, network adapter 1120 communicates with the other components of computer system/server 1112 via bus 1118. It should be understood that although not shown, other hardware and/or software components could be used in conjunction with computer system/server 1112. Examples, include, but are not limited to: microcode, device drivers, redundant processing units, external disk drive arrays, RAID systems, tape drives, and data archival storage systems, etc.

It is understood in advance that although this disclosure includes a detailed description on cloud computing below, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Computing node 1110 in FIG. 11 can be an example of a cloud computing node. Computing node 1110 is only one example of a suitable cloud computing node and is not intended to suggest any limitation as to the scope of use or functionality of embodiments of the invention described herein. Regardless, computing node 1110 is capable of being implemented and/or performing any of the functionality set forth hereinabove. It is also to be understood that computing node 1110 is not necessarily a cloud computing node.

Figure 12:
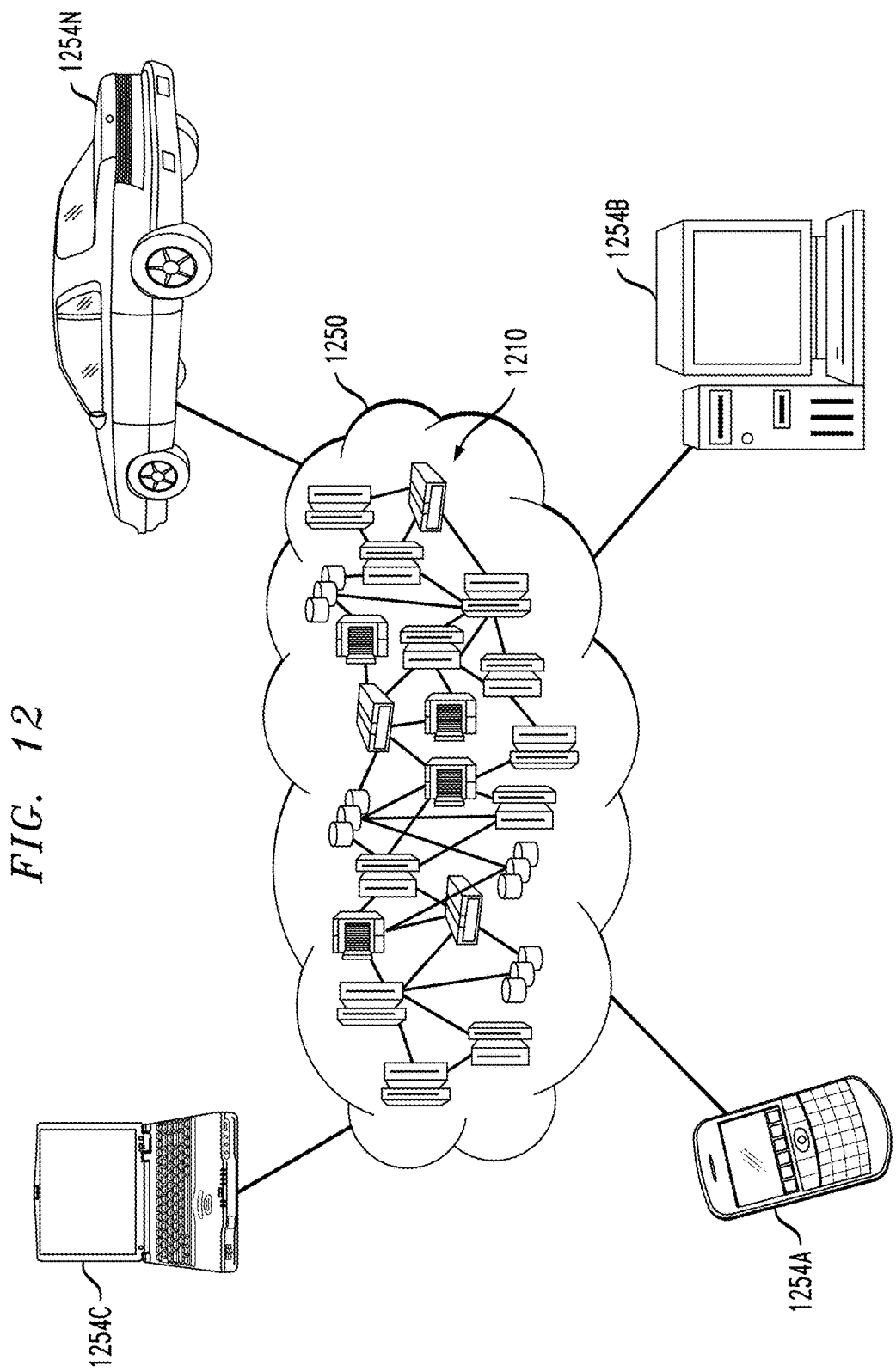
FIG. 12 depicts a cloud computing environment, according to an exemplary embodiment of the present invention.

Referring now to FIG. 12, illustrative cloud computing environment 1250 is depicted. As shown, cloud computing environment 1250 comprises one or more cloud computing nodes 1210 with which local computing devices used by cloud consumers, such as, for example, a wearable device (not explicitly shown), a personal digital assistant (PDA) or cellular telephone 1254A, desktop computer 1254B, laptop computer 1254C, and/or automobile computer system 1254N may communicate. Nodes 1210 may communicate with one another. They may be grouped (not shown) physically or virtually, in one or more networks, such as Private, Community, Public, or Hybrid clouds as described hereinabove, or a combination thereof. This allows cloud computing environment 1250 to offer infrastructure, platforms and/or software as services for which a cloud consumer does not need to maintain resources on a local computing device. It is understood that the types of computing devices 1254A-N shown in FIG. 12 are intended to be illustrative only and that computing nodes 1210 and cloud computing environment 1250 can communicate with any type of computerized device over any type of network and/or network addressable connection (e.g., using a web browser).

Figure 13:
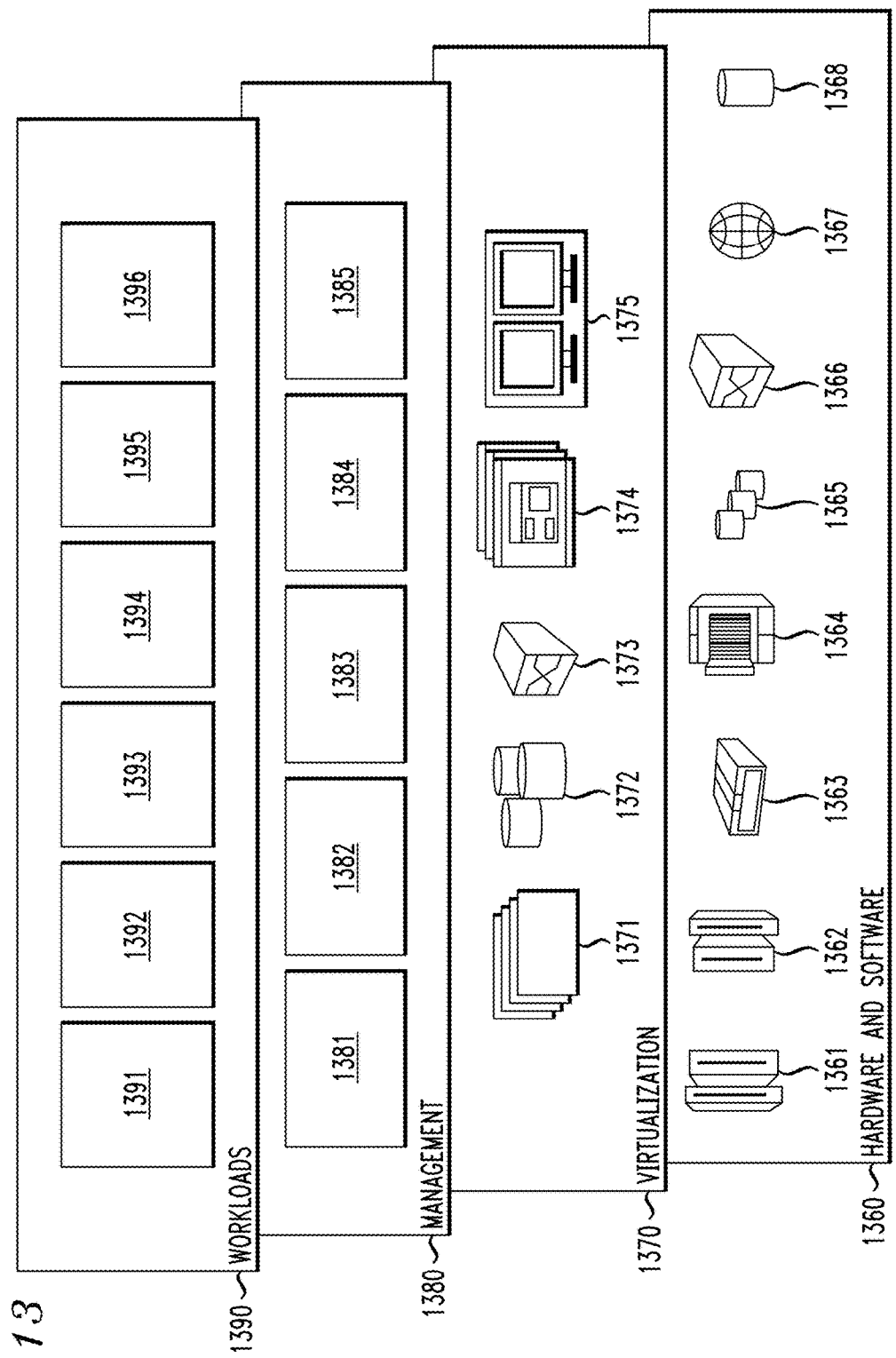
FIG. 13 depicts abstraction model layers, according to an exemplary embodiment of the invention.

Referring now to FIG. 13, a set of functional abstraction layers provided by cloud computing environment 1250 (FIG. 12) is shown. It should be understood in advance that the components, layers, and functions shown in FIG. 13 are intended to be illustrative only and embodiments of the invention are not limited thereto. As depicted, the following layers and corresponding functions are provided:

Hardware and software layer 1360 includes hardware and software components. Examples of hardware components include: mainframes 1361; RISC (Reduced Instruction Set Computer) architecture based servers 1362; servers 1363; blade servers 1364; storage devices 1365; and networks and networking components 1366. In some embodiments, software components include network application server software 1367 and database software 1368.

Virtualization layer 1370 provides an abstraction layer from which the following examples of virtual entities may be provided: virtual servers 1371; virtual storage 1372; virtual networks 1373, including virtual private networks; virtual applications and operating systems 1374; and virtual clients 1375.

In one example, management layer 1380 may provide the functions described below. Resource provisioning 1381 provides dynamic procurement of computing resources and other resources that are utilized to perform tasks within the cloud computing environment. Metering and Pricing 1382 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1383 provides access to the cloud computing environment for consumers and system administrators. Service level management 1384 provides cloud computing resource allocation and management such that required service levels are met. Service Level Agreement (SLA) planning and fulfillment 1385 provide pre-arrangement for, and procurement of, cloud computing resources for which a future requirement is anticipated in accordance with an SLA.

Workloads layer 1390 provides examples of functionality for which the cloud computing environment may be utilized. Examples of workloads and functions which may be provided from this layer include: mapping and navigation 1391; software development and lifecycle management 1392; virtual classroom education delivery 1393; data analytics processing 1394; transaction processing 1395; and patient similarity and risk determination 1396, which may implement the functionality described above with respect to FIGS. 1-12.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

What is claimed is:

1. A method for risk assessment, comprising:
 receiving one or more images of a plurality of lesions captured from a body of a target person;
 generating one or more digital signatures based on the one or more images from the body of the target person;
 comparing the generated one or more digital signatures to digital signatures of respective reference persons, wherein the comparing comprises measuring similarities between the generated one or more digital signatures and the digital signatures of the respective reference persons;
 determining a risk factor for the target person of developing a disease based on the measured similarities and predetermined risk factors of developing the disease for the reference persons;
 separating the reference persons into a plurality of groups based on one or more characteristics of the reference persons; and
 training an auto encoder for each group of the plurality of groups;
 wherein generating the one or more digital signatures comprises processing the one or more images from the body of the target person with each trained auto encoder to generate respective codes corresponding to each trained auto encoder;
 wherein the processing comprises:
  encoding the one or more images from the body of the target person into one or more vectors each having a predetermined size; and
  digitally reconstructing the encoded one or more images into one or more reconstructed images; and
 wherein the method is performed by at least one computer system comprising at least one memory and at least one processor coupled to the memory.

2. The method according to claim 1, wherein the training is performed using lesion images of the reference persons for each group of the plurality of groups.

3. The method according to claim 1, wherein the one or more characteristics are selected from the group comprising age, gender, race, geographic location, behavior, and family history.

4. The method according to claim 1, wherein a digital signature of the one or more digital signatures comprises a matrix of the respective codes.

5. The method according to claim 1, wherein the processing with each trained auto encoder is performed separately for images from different regions on the body of the target person.

6. The method according to claim 1, wherein a digital signature of the one or more digital signatures corresponds to a region on the body of the target person.

7. The method according to claim 1, wherein determining the risk factor for the target person of developing the disease comprises calculating a summation of the predetermined risk factors for each reference person, wherein each of the predetermined risk factors is adjusted based on a value for similarity between the generated one or more digital signatures of the target person and one or more digital signatures of each reference person.

8. The method according to claim 1, wherein measuring the similarities between the generated one or more digital signatures and the digital signatures of the respective reference persons is performed using sparse coding.

9. The method according to claim 8, further comprising defining the generated one or more digital signatures of the target person as a linear combination of the digital signatures of the respective reference persons.

10. A system for risk assessment, comprising:
 a memory and at least one processor coupled to the memory, wherein the at least one processor is configured to:
  receive one or more images of a plurality of lesions captured from a body of a target person;
  generate one or more digital signatures based on the one or more images from the body of a target person;

compare the generated one or more digital signatures to digital signatures of respective reference persons, wherein the processor is further configured to measure similarities between the generated one or more digital signatures and the digital signatures of the respective reference persons;

determine a risk factor for the target person of developing a disease based on the measured similarities and predetermined risk factors of developing the disease for the reference persons;

separate the reference persons into a plurality of groups based on one or more characteristics of the reference persons; and train an auto encoder for each group of the plurality of groups;

wherein in generating the one or more digital signatures, the processor is further configured to process the one or more images from the body of the target person with each trained auto encoder to generate respective codes corresponding to each trained auto encoder;

wherein in processing with each trained auto encoder, the processor is further configured to:
encode the one or more images from the body of the target person into one or more vectors each having a predetermined size; and
digitally reconstruct the encoded one or more images into one or more reconstructed images.

11. The system according to claim 10, wherein a digital signature of the one or more digital signatures comprises a matrix of the respective codes.

12. The system according to claim 10, wherein the processing with each trained auto encoder is performed separately for images from different regions on the body of the target person.

13. The system according to claim 10, wherein a digital signature of the one or more digital signatures corresponds to a region on the body of the target person.

14. The system according to claim 10, wherein:
measuring the similarities between the generated one or more digital signatures and the digital signatures of the respective reference persons is performed using sparse coding; and
the processor is further configured to define the generated one or more digital signatures of the target person as a linear combination of the digital signatures of the respective reference persons.

15. The system according to claim 10, wherein in determining the risk factor for the target person of developing the disease, the processor is further configured to calculate a summation of the predetermined risk factors for each reference person, wherein each of the predetermined risk factors is adjusted based on a value for similarity between the generated one or more digital signatures of the target person and one or more digital signatures of each reference person.

16. A computer program product for risk assessment, the computer program product comprising a computer readable storage medium having program instructions embodied therewith, the program instructions executable by a processor to cause the processor to perform a method comprising:
receiving one or more images of a plurality of lesions captured from a body of a target person;
generating one or more digital signatures based on the one or more images from the body of the target person;
comparing the generated one or more digital signatures to digital signatures of respective reference persons, wherein the comparing comprises measuring similarities between the generated one or more digital signatures and the digital signatures of the respective reference persons;
determining a risk factor for the target person of developing a disease based on the measured similarities and predetermined risk factors of developing the disease for the reference persons;
separating the reference persons into a plurality of groups based on one or more characteristics of the reference persons; and
training an auto encoder for each group of the plurality of groups;
wherein generating the one or more digital signatures comprises processing the one or more images from the body of the target person with each trained auto encoder to generate respective codes corresponding to each trained auto encoder;
wherein the processing comprises:
encoding the one or more images from the body of the target person into one or more vectors each having a predetermined size; and
digitally reconstructing the encoded one or more images into one or more reconstructed images.

* * * * *